(12) United States Patent
Themelis

(10) Patent No.: US 11,978,199 B2
(45) Date of Patent: May 7, 2024

(54) OPTICAL IMAGING SYSTEM AND RELATED APPARATUS, METHOD AND COMPUTER PROGRAM

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

(*) Notice: Subject to any disclaimer, the term of this patent is extended or adjusted under 35 U.S.C. 154(b) by 316 days.

(21) Appl. No.: 17/064,965

(22) Filed: Oct. 7, 2020

(65) Prior Publication Data
US 2021/0110539 A1 Apr. 15, 2021

(30) Foreign Application Priority Data
Oct. 10, 2019 (EP) .................................. 19202516

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/7425* (2013.01); *H04N 23/632* (2023.01); *H04N 23/80* (2023.01); *G06T 2207/30024* (2013.01)

(58) Field of Classification Search
CPC ..... G06T 7/0002; G06T 7/0012; G06T 7/001; G06T 2207/30024; G06T 2207/30004;
(Continued)

(56) References Cited

U.S. PATENT DOCUMENTS 9,072,929 B1 * 7/2015 Rush .................... H04N 13/257
9,648,225 B1 * 5/2017 Preston .................. H04N 23/57
(Continued)

FOREIGN PATENT DOCUMENTS

WO 2008/154935 A1 12/2008
WO 2015/061793 A1 4/2015
WO 2018/095516 A1 5/2018

*Primary Examiner* — Bobbak Safaipour
*Assistant Examiner* — Duy Tran
(74) *Attorney, Agent, or Firm* — SPL Patent Attorneys PartG mbB; Kieran O'Leary

(57) ABSTRACT

Examples relate to an optical system and to an apparatus, method and computer program for an optical system. The optical imaging system comprises a camera for providing a camera image of a surface of an object. The optical imaging system further comprises one or more measurement modules for performing one or more measurements at one or more points of the surface of the object. The optical imaging system further comprises a display module. The optical imaging system further comprises a processing module configured to obtain the camera image of the surface of the object from the camera. The processing module is configured to obtain the one or more measurements at the one or more points of the surface of the object from the one or more measurement modules. The processing module is configured to determine a spatial location of the one or more points of the surface relative to the camera image. The processing module is configured to provide the camera image with an overlay representing the measurements at the one or more points of the surface of the object to the display module.

16 Claims, 3 Drawing Sheets

(51) Int. Cl.
*H04N 5/232* (2006.01)
*H04N 23/63* (2023.01)
*H04N 23/80* (2023.01)

(58) Field of Classification Search
CPC ....... H04N 5/232935; H04N 5/232933; H04N 5/232945; H04N 5/23229; H04N 5/23218; A61B 5/7425; A61B 5/742
See application file for complete search history.

(56) References Cited

U.S. PATENT DOCUMENTS

| | | | |
|---|---|---|---|
| 2012/0038761 A1* | 2/2012 | Sander | A61B 90/20 348/67 |
| 2015/0282749 A1* | 10/2015 | Zand | A61B 5/0084 600/301 |
| 2016/0171711 A1* | 6/2016 | Gopinath | G06T 19/20 382/130 |
| 2016/0248994 A1* | 8/2016 | Liu | A61B 5/7445 |
| 2017/0082847 A1* | 3/2017 | Wilzbach | A61B 34/20 |
| 2018/0070904 A1* | 3/2018 | Yu | G06T 7/73 |

* cited by examiner

OPTICAL IMAGING SYSTEM AND RELATED APPARATUS, METHOD AND COMPUTER PROGRAM

CROSS REFERENCE TO RELATED APPLICATIONS

This application claims priority of European patent application number 19202516.1 filed Oct. 10, 2019, the entire disclosure of which is incorporated by reference herein.

TECHNICAL FIELD

Examples relate to an optical system and to an apparatus, method and computer program for an optical system.

BACKGROUND

In the medical sector, during surgery of a patient, a vast number of technologies exist that may be used to assist the surgeon surgery. For example, a surgeon may use a surgical microscope to examine the tissue on which he or she is operating. Additionally, other means may be used to examine the patient, such as point probes or confocal microscopes, which can be used to gain further insight into the tissue of the patient. Unfortunately, in many cases, the use of multiple technologies at the same time may lead to diminishing returns, as the surgeon might have to consider and remember the specifics of each measurement or test he or she has performed using the different technologies.

SUMMARY

There may be a desired for an improved concept than improves a utility the user of an optical imaging device, such as a surgeon using a surgical microscope, gains from using the optical imaging system together with one or more additional measurement devices.

An embodiment of the present disclosure relates to an optical imaging system. The optical imaging system comprises a camera for providing a camera image of a surface of an object. The optical imaging system further comprises one or more measurement modules for performing one or more measurements at one or more points of the surface of the object. The optical imaging system further comprises a display module. The optical imaging system further comprises a processing module configured to obtain the camera image of the surface of the object from the camera. The processing module is configured to obtain the one or more measurements at the one or more points of the surface of the object from the one or more measurement modules. The processing module is configured to determine a spatial location of the one or more points of the surface relative to the camera image. The processing module is configured to provide the camera image with an overlay representing the measurements at the one or more points of the surface of the object to the display module.

By determining a spatial location of the one or more points of the surface, at which the one or more measurements are taken, relative to the camera image, a spatial relationship between the one or more measurements and the camera image can be derived, and, subsequently, an overlay can be generated that illustrates the one or more measurements relative to the camera image. By creating the overlay, the camera image can be augmented by the measurements, enabling the user to take into account the information originating from the different sources.

An embodiment of the present disclosure relates to an apparatus for an optical imaging system. The apparatus may be used to control the optical imaging device, e.g. with regards to the processing of the camera and measurement data. The apparatus comprises an interface for communicating with a camera, one or more measurements modules and a display module of the optical imaging system. The apparatus comprises a processing module configured to obtain a camera image of a surface of an object from the camera of the optical imaging system. The processing module is configured to obtain one or more measurements at one or more points of the surface of the object from the one or more measurement modules. The processing module is configured to determine a spatial location of the one or more points of the surface relative to the camera image. The processing module is configured to provide the camera image with an overlay representing the measurements at the one or more points of the surface of the object to the display module.

An embodiment of the present disclosure relates to a corresponding method for an optical imaging system. The method comprises obtaining a camera image of a surface of an object from a camera of the optical imaging system. The method comprises obtaining one or more measurements at the one or more points of the surface of the object from one or more measurement modules of the optical imaging system. The method comprises determining a spatial location of the one or more points of the surface relative to the camera image. The method comprises providing the camera image with an overlay representing the measurements at the one or more points of the surface of the object to the display module. An embodiment of the present disclosure relates to a computer program with a program code for performing the method when the computer program is executed on a processor.

BRIEF DESCRIPTION OF THE DRAWING VIEWS

Some examples of apparatuses and/or methods will be described in the following by way of example only, and with reference to the accompanying figures, in which FIG. 1 shows a block diagram of an embodiment of an optical imaging system and of an apparatus for the optical imaging system;

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1:
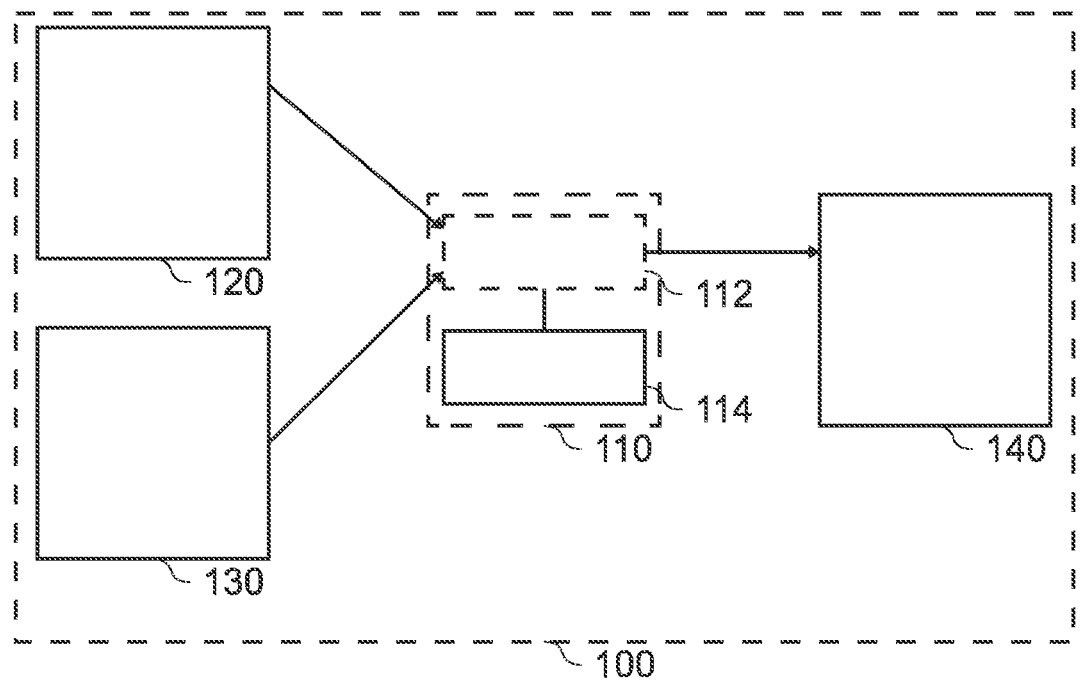

FIG. 1 shows a block diagram of an embodiment of an optical imaging system 100, e.g. of a microscope or surgical microscope 100. The optical imaging system comprises a camera 120 for providing a camera image of a surface of an object. The optical imaging system comprises one or more measurement modules 130 for performing one or more measurements at one or more points of the surface of the object. The optical imaging system comprises a display module 140. The optical imaging system comprises a processing module 114 that is coupled to the camera, the one or more measurement modules and the display module 140, e.g. via an interface 112. FIG. 1 further shows an apparatus 110 comprising the processing module 114 and the interface 112, which is coupled to the processing module 114. The processing module 114 is configured to obtain the camera image of the surface of the object from the camera. The processing module 114 is configured to obtain the one or more measurements at the one or more points of the surface of the object from the one or more measurement modules 130. The processing module 114 is configured to determine a spatial location of the one or more points of the surface relative to the camera image. The processing module 114 is configured to provide the camera image with an overlay representing the measurements at the one or more points of the surface of the object to the display module 140.

Embodiments relate to an optical imaging system, or to an apparatus, method or computer program for an optical imaging system. For example, the optical imaging system may be or may comprise a microscope. For example, the optical imaging system may be a system comprising a microscope, such as a surgical microscope, the camera 120 being the camera of the microscope, and the one or more measurement modules. In other words, the one or more measurement modules may be external to the microscope, and part of the system comprising the microscope. For example, the optical imaging system may be a surgical microscope system or an image guided system. In general, a microscope is an optical instrument that is suitable for examining objects that are too small to be examined by the human eye (alone). For example, a microscope may provide an optical magnification of an object, such as the sample of organic tissue. In modern microscopes, the optical magnification is often provided for a camera or an imaging sensor, such as the camera 120 of the optical imaging system of FIG. 1. In other words, the optical imaging system 100 may further comprise one or more optical magnification components that are used to magnify a view on the object. If the optical imaging system is used in the medical fields, the object may be a sample of organic tissue, e.g. arranged within a petri dish or present in a part of a body. For example, the microscope 100 may be a microscope for use in a laboratory, e.g. a microscope that may be used to examine the sample of organic tissue in a petri dish. Alternatively, the microscope 100 may be part of a surgical microscope system, e.g. a microscope to be used during a surgical procedure. Although embodiments are described in connection with a microscope, they may also be applied, in a more general manner, to any optical device. For example, the optical imaging system may be a system for performing material testing or integrity testing of materials, e.g. of metals or composite materials. In this case, the one or more measurements may be taken at, or of, the material.

The optical imaging system comprises the camera 120. In general, the camera 120 may comprise an imaging sensor, e.g. an APS (Active Pixel Sensor)—or CCD (Charge-Coupled-Device)-based imaging sensor. For example, in APS-based cameras, light is recorded at each pixel using a photodetector and an active amplifier of the pixel. APS-based imaging sensors are often based on CMOS (Complementary Metal-Oxide-Semiconductor) or S-CMOS (Scientific CMOS) technology. In CCD-based imaging sensors, incoming photons are converted into electron charges at a semiconductor-oxide interface, which are subsequently moved between capacitive bins in the imaging sensor modules by a control circuitry of the sensor imaging module to perform the imaging.

The camera 120 is suitable for, or configured to, providing/provide the camera image of the surface of the object. In general, the camera image may be an analog or a digital camera image, i.e. the camera image may be provided as an analog camera signal or as a digital video signal or digital still image. The processing module 114 is configured to obtain the camera image of the surface of the object from the camera. For example, the processing module 114 may be configured to obtain the camera image as an analog camera signal or as a digital video signal or digital still image from the camera, e.g. via a wireless or wirebound connection or via an intermediate storage or memory, e.g. via the interface 112. For example, the camera image may be a two-dimensional pixel-based camera image. In some embodiments, the camera image may be a single image, i.e. a still image. Alternatively, the camera image may be an image of a stream (i.e. a video) of camera images, which are periodically updated. In some embodiments, the term "camera image" may be used for a plurality of (substantially) simultaneously recorded images. For example, the camera image may comprise a "white light" camera image (taken in the entire visible spectrum) and one or more reflectance images and/or fluorescence images (e.g. images, in which one or more wavelength bands are isolated, and which comprise the result of reflectance or fluorescence images as recorded in the one or more wavelength bands). In general, in reflectance imaging, an object is illuminated in a wavelength band, and an image of the object is recorded in the same wavelength band. In fluorescence imaging, the object is illuminated in a first wavelength band, and the image is recorded at a second, different wavelength band.

As laid out before, the object may be a sample of organic tissue, e.g. a sample of organic tissue that is comprised of a part of a body, or a sample of organic tissue that is arranged in a petri dish or on a microscope slide. Consequently, the camera image of the surface of the object may be a camera image showing a top view of the surface of the sample of organic tissue, e.g. a view from outside the sample of organic tissue, as seen from the camera of the microscope. Alternatively, the object may be any other object that is observable through an optical imaging system, e.g. an object that is to be inspected in a material inspection. In this case, the camera image of the surface of the object may show a top view or side view of the object to be examined.

The optical imaging system comprises the one or more measurement modules 130 for performing the one or more measurements at the one or more points of the surface of the object. In general, the one or more measurement modules 130 may be one or more measurement modules suitable for making measurements at a point of the surface of the object, i.e. that indicate a certain property at the point of the surface of the object. In some embodiments, this does not exclude a measurement module that takes a measurement of an area that is larger than a point, but smaller than the surface covered by the camera image, e.g. of an area that is at most 5% (or at most 2%, at most 1%, at most 0.5%, at most 0.2% or at most 0.1%) of the surface covered by the camera image. In other words, the one or more measurements may be taken of an area that covers at most 5% (or at most 2%, at most 1%, at most 0.5%, at most 0.2% or at most 0.1%) of the surface covered by the camera image.

Various measurement means may be used to perform the measurements. For example, the one or more measurements may comprise at least one of one or more optical measurements, one or more electrical measurements, one or more acoustic measurements, one or more mechanical measurements, one or more thermal measurements, one or more tissue sampling measurements, and one or more measurements being based on human sensory reception. For example, the one or more optical measurements may be performed by one or more optical measurement modules, e.g. by one or more of a confocal microscope, a fluorescence imaging module, a reflectance imaging module, a spectroscopy module and a laser ablation module. Accordingly, the one or more optical measurements may comprise one or more of a fluorescence image, a reflectance image, a spectroscopy measurement (e.g. a Raman spectroscopy measurement) and a laser ablation measurement at at least a subset of the one or more points. For example, the one or more electrical measurements may be performed by one or more electrical measurement modules, e.g. by a nerve stimulation module and/or by a potential measurement module. Accordingly, the one or more electrical measurements may comprise one or more of a nerve stimulation measurement and a measurement of potentials at at least a subset of the one or more points. For example, the one or more acoustic measurement may be taken using an ultrasound sensor, for example. Accordingly, the one or more acoustic measurements may comprise one or more ultrasound measurements and/or one or more measurements related to tissue elasticity at at least a subset of the one or more points. For example, the one or more mechanical measurements may be performed by a tactile measurement device. The one or more mechanical measurements may comprise one or more tissue elasticity measurements at at least a subset of the one or more points. For example, the one or more thermal measurements may be taken by one or more thermal measurement modules, e.g. using one or more probes or using one or more optical thermal measurements. The one or more thermal measurements may represent the temperature at at least a subset of the one or more points. For example, the one or more tissue sampling measurements may be taken using a biopsy or mass spectroscopy. The one or more tissue sampling measurements may comprise one or more measurements based on a biopsy at at least a subset of the one or more points or one or more mass spectroscopy measurements at at least a subset of the one or more points. Finally, the one or more measurements, e.g. palpation measurements, being based on human sensory reception may be manually input by a human, e.g. classified by the human and input using a human input interface. For example, the human input interface may be a touch interface or a voice control or dictation interface. In embodiments, a combination of the above measurements may be used for the one or more measurements at the one or more points at the surface at the object.

The processing module is configured to obtain the one or more measurements at the one or more points of the surface of the object from the one or more measurement modules 130. For example, the one or more measurements may be obtained (i.e. received) as analog or digital sensor data from the one or more measurements modules. If human sensory reception is used, at least a subset of the one or more measurements may be obtained via a human interface. In this case, the human interface may be seen one of the one or more measurement modules.

The optical imaging system comprises the display module 140. For example, the display module may be one of a projection-based display module and a screen-based display modules, such as a Liquid Crystal Display (LCD)—or an Organic Light Emitting Diode (OLED)-based display module. The display module 114 may be controlled by the processing module 114, e.g. by a video or control signal provided by the display module. For example, the video or control signal may be based on the camera image and the overlay. In some embodiments, the camera image (or at least a processed version of the camera image) and the overlay may be provided to the display module 140 separately, e.g. as two different video or control signals. Alternatively, the camera image and the overlay may be provided to the display module 140 in combined form, e.g. as a combined video or control signal comprising both the camera image (or at least a processed version of the camera image) and the overlay.

The processing module 114 is configured to determine the spatial location of the one or more points of the surface relative to the camera image. For example, the camera image may represent a portion (i.e. a segment) of the surface of the object. The spatial location of a point of the surface relative to the camera image may represent, where, within the camera image (i.e. the portion of the surface of the object), the point is located, i.e. where, within the portion of the surface of the object, the measurement at the point has been taken. In other words, the one or more points of the surface may be projected onto the camera image, e.g. such that the one or more points are assigned to corresponding locations within the camera image. This assignment may be achieved using various means. For example, at least some of the one or more measurements may be taken using measurement probes. The processing module 114 may be configured to identify a location of one or more probes used to perform the one or more measurements within the camera image to determine the spatial location of the one or more points of the surface relative to the camera image. For example, the processing module 114 may be configured to detect a measurement point of the one more probes within the camera image (e.g. based on an optical marker of the respective probes), and to determine the spatial location of the one or more points based on the location of the measurement point within the camera image, e.g. based on a previous camera image. This may enable the localization of measurements taken using probes.

In some embodiments, at least some of the probes may be equipped with a light source that can be used to track the probe in two-dimensional or three-dimensional space. The light may thereby facilitate a detection of the probe within the camera image. For example, the light source of the respective probe may be used as optical marker of the probe, to enable the localization of the probe as introduced above. The processing module 114 may be configured to identify a location of one or more probes used to perform the one or more measurements using light emitted by one or more light sources attached to the one or more probes to determine the spatial location of the one or more points of the surface relative to the camera image. For example, the processing module 114 may be configured to detect the light emitted by one or more light sources attached to the one or more probes within the camera image (e.g. within a previous camera image), to determine a location of the one or more probes based on the detected light, and to determine the spatial location of the one or more points of the surface relative to the camera image based on the determined location of the one or more probes. Additionally or alternatively, the optical imaging system may comprise one or more additional cameras for tracking the light source of the respective probes. For example, the one or more light sources attached to the one or more probes may be configured to emit infrared light (e.g. near-infrared light), and the processing module 114 may be configured to detect the light emitted by one or more light sources attached to the one or more probes using the one or more additional cameras, the one or additional cameras being cameras for sensing infrared light, to determine a location of the one or more probes based on the detected light, and to determine the spatial location of the one or more points of the surface relative to the camera image based on the determined location of the one or more probes.

In some embodiments, approaches may be chosen that are independent of the camera image. For example, at least a subset of the measurements may be taken using a robotic arm. The orientation of the robotic arm may be known to, or controlled by, the processing module. Based on the orientation of the robotic arm, the spatial location of at least a subset of the one or more measurements may be taken. In other words, the processing module 114 may be configured to determine the spatial location of the one or more points of the surface relative to the camera image based on an orientation of the robotic arm at a time the subset of the one or more measurements are taken.

As laid out above, at least some of the measurements may be taken based on human sensory perception. In this case, the spatial location of the one or more points of the surface relative to the camera image of the respective measurement or measurements may be input manually, or may be detected by the processing module 114 within the camera image, e.g. in response to a voice control of the user/surgeon.

The processing module is configured to provide the camera image with an overlay representing the measurements at the one or more points of the surface of the object to the display module 140. As laid out above, the processing module may be configured to generate a video or control signal for the display module based on the camera image and the overlay, e.g. a combined video or control signal comprising both the camera image and the overlay, or two separate video or control signals, one comprising the camera image and one comprising the overlay. In case a combined video or control signal is used, the processing module may be configured to merge the camera image and the overlay, i.e. the processing module may be configured to add the overlay to the camera image, or to generate a new video signal comprising both the camera image and the overlay. For example, the processing module 114 may be configured to provide the video or control signal to the display module via the interface 112. In any case, the camera image provided to the display module may be or comprise the white light image, or one of the one or more reflectance/fluorescence images, or a combination thereof.

The processing module 114 may be further configured to generate the overlay based on the one or more measurements at the one or more points of the surface of the object and based on the spatial location of the one or more points of the surface relative to the camera image. For example, in a simple embodiment, the processing module 114 may be configured to generate the overlay by generating one or more indicator symbols, indicator colors or numbers representing the one or more measurements at the spatial location of the one or more points of the surface relative to the camera image. For example, thermal readings may be represented by an indicator color or a number, while pathologic tissue may be indicated by a "minus" symbol and healthy tissue may be indicated by a "plus" symbol (or red and green color). The one or more indicator symbols, indicator colors or numbers may be placed within the overlay at the spatial location of the one or more points of the surface relative to the camera image. Such an overlay may be seen in FIG. 3, reference sign 330.

In some embodiments, additional processing may be performed to increase a utility of the overlay. For example, the processing module may be configured to generate the overlay to represent one or more coherent spatial regions, in which similar measurements are grouped. The processing module 114 may be configured to group the one or more measurements into the one or more coherent spatial regions. In this context, "coherent spatial regions" may denote regions within the camera image, which are coherent (i.e. cohesive, without interruptions), and which comprise similar measurements of the one or more measurements. For example, the processing module 114 may be configured to classify the one or more measurements into the one or more groups of similar measurements, or one or more groups of measurements indicating a pre-defined condition, and to generate the one or more coherent spatial regions based on the one or more groups of similar measurements, or one or more groups of measurements indicating a pre-defined condition. The processing module may be configured to provide the camera image with an overlay representing the one or more coherent spatial regions to the display module 140. Such an overlay may be seen in FIG. 3, reference sign 360.

For example, the one or more coherent spatial regions may be determined for a sample of organic tissue. In this case, for example, a distinction between healthy and pathologic (i.e. unhealthy) tissue may be made. In other words, the processing module 114 may be configured to perform a classification of the surface of the sample of organic tissue into healthy and pathologic tissue at the spatial location of the one or more point measurements, e.g. based on the one or more measurements and/or based on the camera image. For example, multiple classes might be used depending on the capabilities of the measuring module. Some modalities have a rather simple classification process, e.g. fluorescence signal above a certain threshold means disease positive, while other require more complicated processing, e.g. confocal images require complicated image analysis or AI (artificial intelligence, e.g. a machine-learning model). For example, the processing module 114 may be configured to perform a classification of the surface of the sample of organic tissue into healthy and pathologic tissue at the spatial location of the one or more point measurements based on the camera image, e.g. based on a fluorescence image included in the camera image. For example, if a brightness within the fluorescence image is above a threshold, diseased/pathologic tissue might be determined. Alternatively or additionally, the processing module 114 may be configured to perform a classification of the surface of the sample of organic tissue into healthy and pathologic tissue at the spatial location of the one or more point measurements based on the one or more measurements. For example, the processing module 114 may be configured to classify, for each point of the one or more points, whether the tissue at the point is deemed healthy or pathologic. The result may be a cloud of classification points spread in 2D space.

The processing module 114 may be configured to group the one or more measurements into two or more coherent spatial regions. The two or more coherent regions may comprise at least one spatial region of healthy tissue and at least one spatial region of pathologic tissue. For example, the processing module 114 may be configured to use the spatial location of the one or more points of the surface relative to the camera image into the different classes (e.g. healthy or pathologic tissue). Furthermore, the processing module 114 may be further configured to, e.g. for each of the one or more points or for each coherent spatial region, a probability or certainty value or map, e.g. to enable surgeons to identify how much they can trust the classification, or whether additional measurements are warranted. The processing module may be configured to use multiple measurements, or the camera image together with the one or more measurements in order to perform the classification. For example, fluorescence imaging, e.g. 5-ALA-induced fluorescence (5-aminolevulinic acid), which may be contained in the camera image, may be indicative of a brain tumor. In addition, a color image may be analyzed with image analysis algorithms, or a machine-learning model. In more general terms, the processing module may be configured to use a machine-learning model to perform the classification of the surface of the sample of organic tissue into healthy and pathologic tissue at the spatial location of the one or more point measurement, e.g. using the camera image and/or the one or more measurements as input to the machine-learning model, and obtaining an output indicating whether the surface at a point of the one or more points is deemed healthy or pathologic.

For example, if the object is a sample of organic tissue, the one or more measurements may comprise at least one of one or more measurements related to a blood oxygen content, one or more measurements related to a tissue perfusion, and one or more measurements related to a temperature of the organic tissue. The processing module 114 may be configured to perform a classification of the surface of the sample of organic tissue into healthy and pathologic tissue at the spatial location of the one or more point measurements based on at least one a blood oxygen content, a tissue perfusion, and a temperature at the spatial location of the one or more point measurements. This classification may be subsequently used to determine the two or more coherent spatial regions. For example, at least one of the two or more spatial regions may indicate healthy tissue and/or at least one of the two or more spatial regions may indicate pathologic tissue.

In at least some embodiments, the camera image and/or the one or more measurements may be used to create and visualize a map, which may be used as the overlay. For example, the map may include the points where measurements were taken with the one or more measurement modules. The location markings may also indicate the classification result, i.e. healthy or diseased tissue. The classification may be indicated with symbols, colors, or time modulated signs. Additionally or alternatively, the map may comprise a classification of the one or more coherent spatial regions. One way to do it is with a "color-heat map" similar to the one used for weather/temperature forecasts, i.e. it could use green and red colors for healthy and diseased tissue accordingly, while the transparency level may vary according to the confidence, transparent denoting less confident, and deep color with not transparency denoting high certainty.

In organic tissue, anatomical features may be found, such as blood vessels, fat tissue, bones, tumors etc. Often, measurements may be similar within the anatomical features— for example, a blood oxygen content may be similar at various points of a blood vessel, as may the temperature. Therefore, the one or more coherent regions may be mapped to corresponding coherent regions (representing the anatomical features) within the camera image. For example, the processing module 114 may be configured to determine one or more coherent regions within the camera image. For example, the one or more coherent regions may represent one or more anatomical features of the sample of organic tissue. The processing module 114 may be configured to group the one or more measurements into the one or more coherent spatial regions further based on the one or more coherent regions within the camera image. For example, the coherent spatial regions to be overlaid on the camera image may be aligned to the one or more coherent regions within the camera image. This may provide additional context to the measurements.

In some embodiments, measurements are taken within a scale of values, e.g. a value-based scale. For example, a blood oxygen content may be measured in percent on a percentage scale, a temperature may be measured on a centigrade (or Fahrenheit) scale. Such values may e.g. be represented by colors within the overlay, with a color representing a value within the scale of values. In some embodiments, the colors may be placed as color dots at the spatial location of the one or more points relative to the camera image. To provide an improved overview, values between the one or more points may be interpolated, enabling the surgeon to more immediately grasp transitions within the measurements. For example, the processing module 114 may be configured to determine (i.e. estimate and/or interpolate) one or more intermediate values for spatial locations located between the one or more points of the surface based on the one or more measurements. For example, the processing module 114 may be configured to determine the one or more intermediate values for the spatial locations located between the one or more points of the surface based on a grid spanning the camera image, i.e. for points on the grid. The processing module 114 may be configured to determine the one or more intermediate values by (linearly) interpolating or estimating the one or more intermediate values based on the one or more measurements, e.g. based on the spatial location of the one or more points at which the one or more measurements have been performed. The processing module 114 may be configured to provide the camera image with an overlay representing the one or more measurements and the one or more intermediate values within a continuous spectrum, e.g. within a continuous color spectrum being used to represent the one or more measurements and the one or more intermediate values.

In some embodiments, the distribution of the one or more points at the surface of the object may be analyzed to determine, how the one or more measurements can be augmented with additional measurements. For example, it may be useful to perform additional measurements at anatomical features that have not been probed before, or to perform additional measurements at "holes" within the one or more measurements, e.g. between measurements indicating healthy and pathologic tissue, respectively. The processing module 114 may be configured to determine a distribution of the one or more points at the surface of the object. For example, the processing module 114 may be configured to determine at least one of a local density of the distribution, a uniformity of the distribution and one or more gaps within the distribution of the one or more points at the surface of the object. The processing module 114 may be configured to determine one or more additional points of the surface of the object (e.g. a scanning path) warranting one or more additional measurements at the surface of the object based on the distribution of the one or more points at the surface of the object. For example, the processing module 114 may be configured to the determine one or more additional points of the surface of the object warranting one or more additional measurements at the surface of the object such, that a local density of the distribution is improved, a uniformity of the distribution is improved, and/or the one or more gaps within the distribution are reduced or closed. For example, the one or more additional points of the surface of the object warranting one or more additional measurements may be points, at which measurements may be performed in order to improve at least one of the above criteria.

In some embodiments, the one or more additional points of the surface of the object warranting one or more additional measurements at the surface of the objects may be determined based on the one or more coherent regions within the camera image. If, for example, sufficient measurements exist for a coherent region, this coherent region might not yield additional points that warrant additional measurements. On the other hand, if a further coherent region comprises few or no measurement, additional measurements may be performed within that region. Additionally or alternatively, additional measurements may be warranted in regions, in which a border of a disease is to be determined. In other words, the processing module 114 may be configured to determine the one or more additional points of the surface of the object warranting one or more additional measurements at the surface of the objects further based on the one or more coherent regions within the camera image, e.g. such that the one or more additional points are determined for regions of the one or more coherent regions with an insufficient number or distribution of measurements. This may improve an effectiveness of the additional measurements, as the measurements might be taken where they are needed most.

The interface 112 may correspond to one or more inputs and/or outputs for receiving and/or transmitting information, which may be in digital (bit) values according to a specified code, within a module, between modules or between modules of different entities. For example, the interface 12 may comprise interface circuitry configured to receive and/or transmit information. In embodiments the processing module 114 may be implemented using one or more processing units, one or more processing devices, any means for processing, such as a processor, a computer or a programmable hardware component being operable with accordingly adapted software. In other words, the described function of the processing module 114 may as well be implemented in software, which is then executed on one or more programmable hardware components. Such hardware components may comprise a general purpose processor, a Digital Signal Processor (DSP), a micro-controller, etc.

More details and aspects of the optical imaging system or the apparatus for the optical imaging system are mentioned in connection with the proposed concept or one or more examples described above or below (e.g. FIG. 2 or 3). The optical imaging system or the apparatus for the optical imaging system may comprise one or more additional optional features corresponding to one or more aspects of the proposed concept or one or more examples described above or below.

Figure 2:
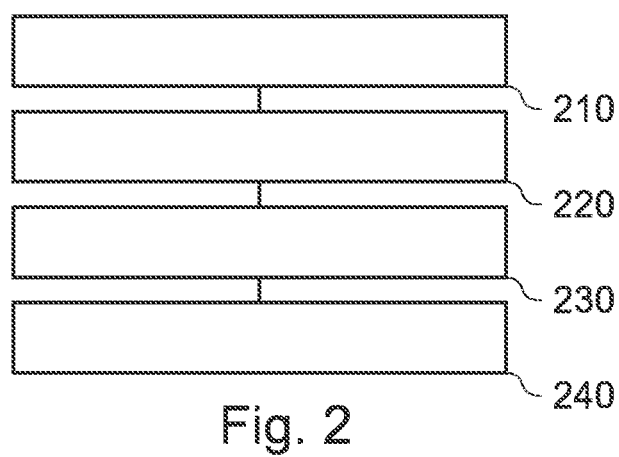
FIG. 2 shows a flow chart of an embodiment of a method for an optical imaging system.

FIG. 2 shows a flow chart of an embodiment of a corresponding method, e.g. a computer-implemented method, for an optical imaging system, e.g. the optical imaging system 100 of FIG. 1. Although the aspects of the optical imaging system have been described in the context of an apparatus, it is clear that these aspects also represent a description of the corresponding method, where a property or functional feature of the apparatus corresponds to a method step or a feature of a method step. The method comprises obtaining 210 a camera image of a surface of an object from a camera of the optical imaging system 100. The method comprises obtaining 220 one or more measurements at the one or more points of the surface of the object from one or more measurement modules 130 of the optical imaging system 100. The method comprises determining 230 a spatial location of the one or more points of the surface relative to the camera image. The method comprises providing 240 the camera image with an overlay representing the measurements at the one or more points of the surface of the object to the display module 140.

As indicated above, features described in connection with the optical imaging system 100 of FIG. 1 may be likewise applied to the method of FIG. 2.

More details and aspects of the method are mentioned in connection with the proposed concept or one or more examples described above or below (e.g. FIG. 1 or 3). The method may comprise one or more additional optional features corresponding to one or more aspects of the proposed concept or one or more examples described above or below.

At least some embodiments of the present disclosure relate to a concept for tracking point measurements and providing a corresponding visual mapping. Embodiments may be based on collecting and visualizing different measurement data (e.g. the one or more measurements), especially point measurements such as confocal microscope results.

Various diagnostic modalities may be used in parallel to the surgical microscope to provide additional information. For example, the one or more measurement modules may comprise one or more of the following diagnostic modalities. These modalities could be point measurements or imaging compared to the field of view of the microscope. For example, both ultrasound and confocal microscope can provide images, but the sampling/imaging areas are significantly different dimensions. For example, ultrasound (US) provides images with dimension which can be compared to the microscope's FOV, and therefore the US image can be overlaid to the optical image, even if the dimensions are not the same. However, confocal microscope (CM) may be aimed at seeing cell morphology, and therefore may have a much higher magnification than the surgical microscope. As a result, typically, a CM image (typical diameter 0.5 mm) only covers a few pixels of the surgical microscope image (typical diameter 20 mm). In this example, the CM image may be a measurement of the one or more measurements, and the surgical microscope image may be the camera image. Essentially, the CM measurements, although technically are images, are only used as point measurements in the context of the surgical microscope image. A CM image can inform about the pathology of the sampling area, i.e. healthy or diseased, without providing any spatial information about how the disease is distributed within the microscope image. Thereby, multiple CM measurements may be used in order to acquire some information of the healthy and/or disease spatial distributions, i.e. disease borders. For example, other modalities may include various spectroscopy types such as fluorescence, reflectance, Raman, laser ablation, and polarization or nerve stimulation electrodes.

In some systems, point measurements are used as a random sampling tool, without any recording of the locations and corresponding findings. The process is similar to metal-detectors which beep when above ground which contains a metal, but do not provide a map. Therefore, the surgeon may try to remember the measurement results and may thereby create in his head some perception of the spatial distribution. This may be less than ideal, as the virtual mapping in surgeon's mind may be very rough, and prone to mistakes. Furthermore, this information might not be saved, and it may be difficult to remember even during the operation. Furthermore, the spatial sampling of the tissue may be rather random as it may be hard to remember where previous measurements are taken. Furthermore, a correlation between different modalities may be very difficult. For example it may be hard to cross check a fluorescence image and multiple CM results.

Embodiments of the present disclosure propose a method and system for collecting, visualizing, and storing point measurements. The system may comprise at least some of the following components:

First, the system, e.g. the optical imaging system, may comprise one or more measurement modalities, e.g. the camera and the one or more measurements modules. For once, the system may comprise a camera, typically the microscope's main camera. Additionally, the system may comprise further one or more measurement modalities, typically one or more point measurement device. In other words, at least a subset of the one or more measurements modules may be point measurement modules. Measurement modalities may include one or more of:

Optical modalities, e.g. fluorescence, reflectance, spectroscopy, laser ablation
Electrical, e.g. nerve stimulation and measurement of potentials
Acoustic, e.g. ultrasound
Mechanical, e.g. tissue elasticity (this can also be measured with acoustic measurements)
Thermal (thermal measurements can also be taken optically)
Tissue sampling, e.g. biopsy, mass spectroscopy
Human sensory, e.g. palpation, and classification is done by human manually, per point The system may further comprise a processing unit, e.g. the processing module or the apparatus 110, which may collect the data from the measurement modalities. For example, the processing unit may comprise one or more of the following features:

The point measurements may be taken with synchronous measurement of spatial coordinates relative to the microscope camera captured-image. For example, this can be done by:

Using the microscope camera which can see the tissue and the point-measurement probe, and therefore can record the position of the tip at the time point of the measurement.

Use of an external position-measurement system which provides information of the measurement tip. This can be easily done by 3 or more NIR (Near Infra-Red) LEDs attached on the probe, and NIR cameras.

By using a robotic arm which scans with the probe tip the tissue surface. The robot can provide the coordinates of tissue in space.

The point measurements may be processed to result a tissue classification such as healthy and diseased (i.e. pathologic), e.g. as a precursor to determine the one or more coherent spatial regions. Multiple classes might be used depending on the capabilities of the measuring modality. Some modalities have a rather simple classification processes, e.g. fluorescence signal above a certain threshold means disease positive, while other require more complicated processing, e.g. confocal images require complicated image analysis or AI (artificial intelligence). The result may be a cloud of classification points spread in 2D space.

The processing unit (i.e. a processor) may use the spatial distribution of the measurements to segment the 2D space into the different classes used, e.g. into the one or more coherent spatial regions. In the simplest case into healthy and diseased areas. This segmentation could also include a probability or certainty map, so that the surgeons may know how much they can trust the calculated maps, or if additional measurements are needed.

In some embodiments, the processing unit might also propose sampling locations or scanning paths in order to clarify the most ambiguous areas. Thereby, it may reduce the workload of the surgeon, and improve the efficiency of the process.

The processing unit may use multiple diagnostic data in order to perform the classification. For example the following data could be used for a combined evaluation. For example, fluorescence imaging, e.g. 5-ALA-induced fluorescence, may be indicative of a brain tumor. In addition, a color image may be analyzed with image analysis algorithms, or AI (e.g. a machine-learning model).

In at least some embodiments, the captured data may be used to create and visualize a map, which may be used as overlay. For example, the map may include any of the following data. For example, the map may include an image of the tissue, e.g. the camera image. This image might typically be a color image showing the tissue anatomy. However, it might also be any combination of color, fluorescence, multispectral images. Additionally (or alternatively), the map may include the points where measurements were taken with the point measurement modality. The location markings may also indicate the diagnostic result, i.e.

healthy or diseased tissue. It may be done with symbols, colors, or time modulated signs. Additionally or alternatively, the map may comprise a classification of the image areas, e.g. the one or more coherent spatial regions. One way to do it is with a "color-heat map" similar to the one used for weather/temperature forecasts, i.e. it could use green and red colors for healthy and diseased tissue accordingly, while the transparency level may vary according to the confidence, transparent means less confident, and deep color with not transparency means high certainty.

Figure 3:
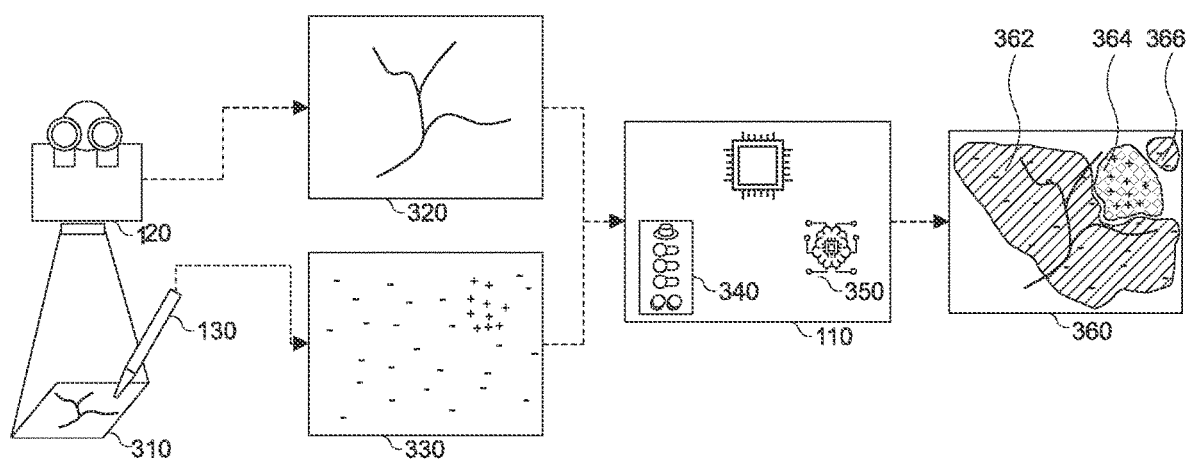
FIG. 3 shows a block diagram of an overlay generated by a processing unit according to an embodiment.

FIG. 3 shows a block diagram of an overlay generated by a processing unit according to an embodiment. In the system of FIG. 3, a camera 120 of a surgical microscope is used to generate a camera image 320 of a surface of a sample of organic tissue. At the same time, a point measuring modality 130 (e.g. a measurement module) is used at the tissue 310 to take one or more measurements 330. In the map shown at reference sign 330, disease-positive measurements are indicated by a plus sign, and disease-negative measurements are indicated by a minus sign. Both the camera image and the measurements are provided to a processing unit 110 (e.g. the apparatus 110 comprising the processing module 114). Based on user settings 340 and artificial intelligence 350 (e.g. a machine-learning model), the processing unit may generate a combined image 360, that is based on the camera image 320 and the map of measurements 330, and in which coherent spatial regions 362, 364, 366 are shown overlaid over the camera image, the coherent spatial regions indicating healthy (362, 366) and diseased (364) tissue.

More details and aspects of the concepts shown in connection with FIG. 3 are mentioned in connection with the proposed concept or one or more examples described above or below (e.g. FIGS. 1 and/or 2). The concepts shown in connection with FIG. 3 may comprise one or more additional optional features corresponding to one or more aspects of the proposed concept or one or more examples described above or below.

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g. sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g. a classification algorithm, a regression algorithm or a similarity learning algorithm. Classification algorithms may be used when the outputs are restricted to a limited set of values (categorical variables), i.e. the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning, (only) input data might be supplied and an unsupervised learning algorithm may be used to find structure in the input data (e.g. by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input but also transform it in a way that makes it useful, often as a preprocessing step before performing classification or predictions. Feature learning may be based on principal components analysis or cluster analysis, for example.

In some examples, anomaly detection (i.e. outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge (e.g. based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g. of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e. support vector networks) are supervised learning models with associated learning algorithms that may be used to analyze data (e.g. in classification or regression analysis). Support vector machines may be trained by providing an input with a plurality of training input values that belong to one of two categories. The support vector machine may be trained to assign a new input value to one of the two categories.

Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

Figure 4:
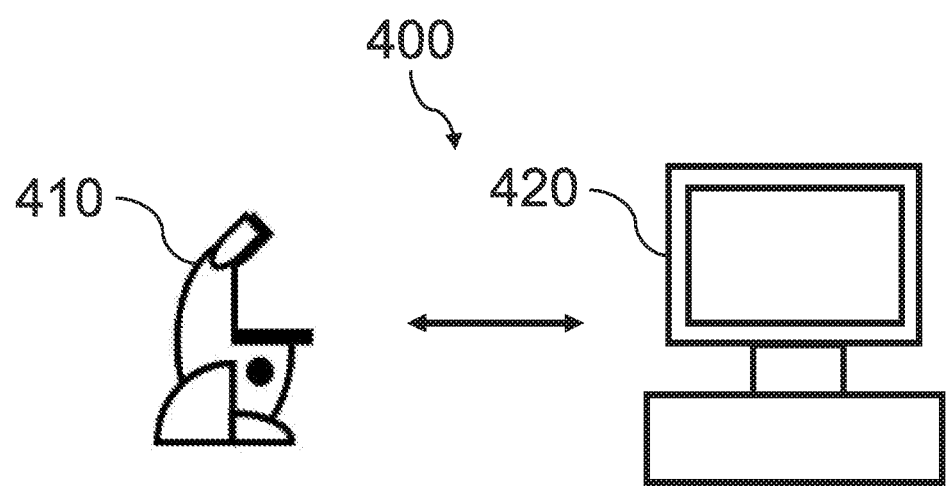
FIG. 4 shows a schematic diagram of a system comprising a microscope or optical imaging system and a computer system.

Some embodiments relate to a microscope or optical imaging system comprising a system as described in connection with one or more of the FIGS. 1a to 3. Alternatively, a microscope or optical imaging system may be part of or connected to a system as described in connection with one or more of the FIGS. 1a to 3. FIG. 4 shows a schematic illustration of a system 400 configured to perform a method described herein. The system 400 comprises a microscope or optical imaging system 410 and a computer system 420. The microscope or optical imaging system 410 is configured to take images and is connected to the computer system 420. The computer system 420 is configured to execute at least a part of a method described herein. The computer system 420 may be configured to execute a machine learning algorithm. The computer system 420 and microscope or optical imaging system 410 may be separate entities but can also be integrated together in one common housing. The computer system 420 may be part of a central processing system of the microscope or optical imaging system 410 and/or the computer system 420 may be part of a subcomponent of the microscope or optical imaging system 410, such as a sensor, an actor, a camera or an illumination unit, etc. of the microscope or optical imaging system 410.

The computer system 420 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 420 may comprise any circuit or combination of circuits. In one embodiment, the computer system 420 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or optical imaging system or a microscope or optical imaging system component (e.g. camera) or any other type of processor or processing circuit. Other types of circuits that may be included in the computer system 420 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 420 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 420 may also include a display device, one or more speakers, and a keyboard and/or controller, which can include a mouse, trackball, touch screen, voice-recognition device, or any other device that permits a system user to input information into and receive information from the computer system 420.

More details and aspects of the system, of the microscope or optical imaging system and/or of the computer system are mentioned in connection with the proposed concept or one or more examples described above or below (e.g. FIG. 1a to 3). The system, microscope or optical imaging system or computer system may comprise one or more additional optional features corresponding to one or more aspects of the proposed concept or one or more examples described above or below.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

100 Optical imaging system
110 Apparatus for an optical imaging system
112 Interface
114 Processing module
120 Camera
130 One or more measurements modules
140 Display module
210 Obtaining a camera image
220 Obtaining one or more measurements
230 Determining a spatial location
240 Providing the camera image
310 Tissue
320 Camera image
330 Map of one or more measurements
340 User settings
350 Artificial Intelligence
360 Combined image
362 Healthy tissue
364 Pathologic tissue
366 Healthy tissue
400 System
410 Microscope or optical imaging system
420 Computer system

What is claimed is:
1. An optical imaging system comprising:
a camera for providing a camera image of a surface of an object;
one or more measurers for performing one or more measurements at one or more points of the surface of the object;
a display; and
a processor configured to:
obtain the camera image of the surface of the object from the camera, obtain the one or more measurements at the one or more points of the surface of the object from the one or more measurers,
determine a spatial location of the one or more points of the surface relative to the camera image,
determine one or more intermediate values for spatial locations located between the one or more points of the surface based on the one or more measurements, wherein the intermediate values are based on the one or more measurements,
generate a combined image based on the camera image and the spatial location of the one or more points by:
determining one or more coherent anatomical regions within the camera image;
grouping the one or more measurements into one or more coherent spatial regions by grouping similar measurements; and
mapping the one or more coherent spatial regions to corresponding one or
more coherent anatomical regions within the camera image, and
provide the combined image with an overlay representing the measurements at the one or more points of the surface of the object and the one or more intermediate values within a continuous spectrum to the display, the overlay representing the one or more coherent spatial regions.

2. The optical imaging system according to claim 1, wherein the object is a sample of organic tissue, wherein the processor is configured to perform a classification of the surface of the sample of organic tissue into healthy and pathologic tissue at the spatial location of the one or more points of the surface of the object, and to group the one or more measurements into two or more coherent spatial regions, the two or more coherent spatial regions comprising at least one spatial region of healthy tissue and at least one spatial region of pathologic tissue.

3. The optical imaging system according to claim 1, wherein the processor is configured to identify a location of one or more probes used to perform the one or more measurements within the camera image to determine the spatial location of the one or more points of the surface relative to the camera image.

4. The optical imaging system according to claim 1, wherein the processor is configured to identify a location of one or more probes used to perform the one or more measurements using light emitted by one or more light sources attached to the one or more probes to determine the spatial location of the one or more points of the surface relative to the camera image.

5. The optical imaging system according to claim 1, wherein at least a subset of the one or more measurements are taken using a robotic arm, the processor is configured to determine the spatial location of the one or more points of the surface relative to the camera image based on an orientation of the robotic arm at a time the subset of the one or more measurements are taken.

6. The optical imaging system according to claim 1, wherein the processor is configured to determine a distribution of the one or more points at the surface of the object, and to determine one or more additional points of the surface of the object warranting one or more additional measurements at the surface of the object based on the distribution of the one or more points at the surface of the object.

7. The optical imaging system according to claim 6, wherein the processor is configured to determine one or more coherent regions within the camera image, and to determine the one or more additional points of the surface of the object warranting one or more additional measurements at the surface of the objects further based on the one or more coherent regions within the camera image.

8. The optical imaging system according to claim 1, wherein the one or more measurements comprise at least one of: an optical measurement, an electrical measurement, an acoustic measurement, a mechanical measurement, a thermal measurement, a tissue sampling measurement, and a measurement based on human sensory reception.

9. The optical imaging system according to claim 1, wherein the object is a sample of organic tissue, wherein the one or more measurements comprise at least one of: a measurement related to a blood oxygen content, a measurement related to a tissue perfusion, and a measurement related to a temperature of the organic tissue.

10. The optical imaging system of claim 1, wherein the processor is configured to generate the combined image based on the camera image and the spatial location of the one or more points using a machine-learning model.

11. An apparatus for an optical imaging system, the apparatus comprising:
an interface for communicating with a camera, one or more measurers and a display of the optical imaging system; and
a processor configured to:
obtain a camera image of a surface of an object from the camera of the optical imaging system;
obtain one or more measurements at one or more points of the surface of the object from the one or more measurers,
determine a spatial location of the one or more points of the surface relative to the camera image,
determine a distribution of the one or more points at the surface of the object, and to determine one or more additional points of the surface of the object warranting one or more additional measurements at the surface of the object based on the distribution of the one or more points at the surface of the object,
generate a combined image based on the camera image and the spatial location of the one or more points by:
determining one or more coherent anatomical regions within the camera image;
grouping the one or more measurements into one or more coherent spatial regions by grouping similar measurements; and
mapping the one or more coherent spatial regions to corresponding one or more coherent anatomical regions within the camera image, and
provide the combined image with an overlay representing the measurements at the one or more points of the surface of the object to the display, the overlay representing the one or more coherent spatial regions.

12. The apparatus of claim 11, wherein the processor is configured to generate the combined image based on the camera image and the spatial location of the one or more points using a machine-learning model.

13. The apparatus of claim 11, wherein the processor is further configured to generate the combined image based on the spatial location of the one or more additional points.

14. A method for an optical imaging system, the method comprising:
obtaining a camera image of a surface of an object from a camera of the optical imaging system;

obtaining one or more measurements at the one or more points of the surface of the object from one or more measurers of the optical imaging system;

determining a spatial location of the one or more points of the surface relative to the camera image;

determining one or more intermediate values for spatial locations located between the one or more points of the surface based on the one or more measurements, wherein the intermediate values are based on the one or more measurements;

generating a combined image based on the camera image and the spatial location of the one or more points by:

determining one or more coherent anatomical regions within the camera image, grouping the one or more measurements into one or more coherent spatial regions by grouping similar measurements, and mapping the one or more coherent spatial regions to corresponding one or more coherent anatomical regions within the camera image; and providing the combined image with an overlay representing the measurements at the one or more points of the surface of the object and the one or more intermediate values within a continuous spectrum to the display, the overlay representing the one or more coherent spatial regions.

15. A non-transitory computer-readable medium storing a computer program comprising instructions which, when the instructions are executed by a processor, cause the processor to perform the method according to claim 14.

16. The method of claim 14, wherein generating the combined image based on the camera image and the spatial location of the one or more points uses a machine-learning model.

* * * * *